United States Patent
Sakai et al.

(10) Patent No.: US 9,518,847 B2
(45) Date of Patent: Dec. 13, 2016

(54) LIGHT GUIDE SENSOR, AND METHOD OF FORMING LIGHT GUIDE SENSOR

(71) Applicant: OLYMPUS CORPORATION, Tokyo (JP)

(72) Inventors: Aiko Sakai, Higashimurayama (JP); Takeshi Ito, Hino (JP); Jun Hane, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 73 days.

(21) Appl. No.: 14/570,388

(22) Filed: Dec. 15, 2014

(65) Prior Publication Data
US 2015/0097110 A1   Apr. 9, 2015

Related U.S. Application Data

(63) Continuation of application No. PCT/JP2013/066870, filed on Jun. 19, 2013.

(30) Foreign Application Priority Data

Jun. 21, 2012   (JP) ................... 2012-139802

(51) Int. Cl.
*G01D 5/353* (2006.01)
*G01B 11/16* (2006.01)

(52) U.S. Cl.
CPC ............. *G01D 5/3537* (2013.01); *G01B 11/18* (2013.01); *G01D 5/3538* (2013.01); *G01D 5/35354* (2013.01); *G01D 5/35374* (2013.01)

(58) Field of Classification Search
CPC ............. G01D 5/3537; G01D 5/35374; G01D 5/35354; G01B 11/18
See application file for complete search history.

(56) References Cited

U.S. PATENT DOCUMENTS 5,631,559 A   5/1997   Oliver et al.
5,633,494 A   5/1997   Danisch
(Continued)

FOREIGN PATENT DOCUMENTS

JP   57-141604 A   9/1982
JP   H08-511343 A   11/1996
(Continued)

OTHER PUBLICATIONS

Extended Supplementary European Search Report dated Feb. 29, 2016 from related European Application No. 13 80 6619.6.
(Continued)

*Primary Examiner* — Tony Ko
(74) *Attorney, Agent, or Firm* — Scully, Scott, Murphy & Presser, P.C.

(57) ABSTRACT

A light guide sensor includes a light source, a light guide member comprising a core which guides light radiated from the light source, a cladding formed around the core, and at least one detecting portion is formed, and a light receiving unit which receives the light that has been guided by the member and has passed via the detecting portion. The detecting portion includes a first opening formed by removal in the outer circumference of the member so that at least part of the cladding is left by a thickness such as not to transmit the light from the core, and a second opening formed within the range of the first opening to transmit the light from the core. A method of forming such a light guide sensor is provided.

22 Claims, 5 Drawing Sheets

A-A (56) References Cited

U.S. PATENT DOCUMENTS 7,060,964 B1     6/2006   Pi et al.
8,886,001 B2 * 11/2014   Kersey .................. G01B 11/18
                                                                           385/123

FOREIGN PATENT DOCUMENTS

| JP | 2006-301178 A | 11/2006 |
|---|---|---|
| JP | 4005318 B2 | 11/2007 |
| JP | 2013-036925 A | 2/2013 |
| WO | WO 2011/067908 A1 | 6/2011 |

OTHER PUBLICATIONS

English translation of International Preliminary Report on Patentability together with the Written Opinion dated Dec. 31, 2014 received in related International Application No. PCT/JP2013/066870.
International Search Report dated Jul. 23, 2013 issued in PCT/JP2013/066870.
English Abstract of WO 94/29671 A1, dated Dec. 22, 1994.
English Abstract of JP 2002-253481 A, dated Sep. 10, 2002.
Japanese Office Action dated Apr. 26, 2016 in related Japanese Patent Application No. 2012-139802.
Chinese Office Action dated Jun. 3, 2016 in related Chinese Patent Application No. 2013800326122.

* cited by examiner

LIGHT GUIDE SENSOR, AND METHOD OF FORMING LIGHT GUIDE SENSOR

CROSS-REFERENCE TO RELATED APPLICATIONS

This application is a Continuation Application of PCT Application No. PCT/JP2013/066870, filed Jun. 19, 2013 and based upon and claiming the benefit of priority from prior the Japanese Patent Application No. 2012-139802, filed Jun. 21, 2012, the entire contents of all of which are incorporated herein by references.

BACKGROUND OF THE INVENTION

1. Field of the Invention

The present invention relates to a light guide sensor which detects a curve by a change in light amount, and a method of forming the light guide sensor.

2. Description of the Related Art

A light guide sensor is generally known as a device which detects the bending and twisting of a flexible measurement target. The light guide sensor is, for example, a fiber sensor, and comprises a light source, an optical fiber having a core and a cladding which guide at least light, and a light receiving unit.

For example, Japanese Patent No. 4005318 has disclosed a flexible endoscope device comprising a curve detection optical fiber (detection light guide member) which is a fiber sensor having more than one curve detecting portion (optical characteristic converting portion). These optical characteristic converting portions are, for example, light absorption portions or light guide loss portions which are small defective portions where the core is exposed. The detection light guide member is disposed at a predetermined position on the surface of one flexible strip member extending in the longitudinal direction of an endoscope insertion portion. In this instance, the curve detecting portions are arranged at predetermined intervals in the longitudinal direction of the strip member, and the same curve detecting portions are arranged side by side in the lateral direction.

The optical characteristic converting portions formed in the detection light guide member have the function to lose light in accordance with the direction and degree of bending and twisting of an insertion portion flexible tube of a measurement target, for example, a flexible endoscope. That is, the direction and degree of bending are detected by the change of the light transmission amount in at least one optical characteristic converting portion arranged in the longitudinal direction. Moreover, in the event of twisting, the light transmission amount varies according to the successively arranged optical characteristic converting portions, and the direction and degree of twisting are detected by the variation of the light transmission amount.

BRIEF SUMMARY OF THE INVENTION

According to an embodiment of the present invention, there is provided a light guide sensor comprising: a light source, a light guide member comprising a core which guides light radiated from the light source, a cladding formed around the core, and at least one detecting portion, and a light receiving unit which receives the light that has been guided by the light guide member and has passed via the detecting portion, wherein the detecting portion comprises a first opening which is formed by removal in the outer circumference of the light guide member so that at least part of the cladding is left by a thickness such as not to transmit the light from the core, and a second opening which is formed within the range of the first opening to transmit the light from the core.

According to another embodiment of the present invention, there is provided a method of forming a detecting portion of a light guide sensor, the light guide sensor comprising a flexible light guide member comprising a core which guides light radiated from a light source and a cladding surrounding the core, at least one detecting portion is formed in the cladding and is disposed at a detection position of a measurement target; and a light receiving unit which receives the light guided by the light guide member, the method characterized by comprising forming a first opening by deforming at least part of the cladding into a recessed shape to leave a thickness such as not to transmit light at a position to be the detecting portion and forming a second opening deformed into a recessed shape to transmit the light from the core within the range of the first opening.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE PREFERRED EMBODIMENT

Hereinafter, embodiments of the present invention will be described with reference to the drawings.

[First Embodiment]

A light guide sensor 1 is, for example, integrally attached along a measurement target which is a long and flexible member, and thereby detects the bending state and bending direction of the measurement target. The curved part of the measurement target is aligned with the light guide sensor 1 when the light guide sensor 1 is attached to the measurement target, and a detecting portion 60 is thereby disposed at a proper position of the measurement target. An article or the like to which the light guide sensor 1 is attached is hereinafter also referred to as the measurement target. The proper position is a position suited to detect the bending state and/or bending direction of the measurement target, that is, a designed or specified position. Hereinafter, the proper position is referred to as the specified position.

Figure 1:
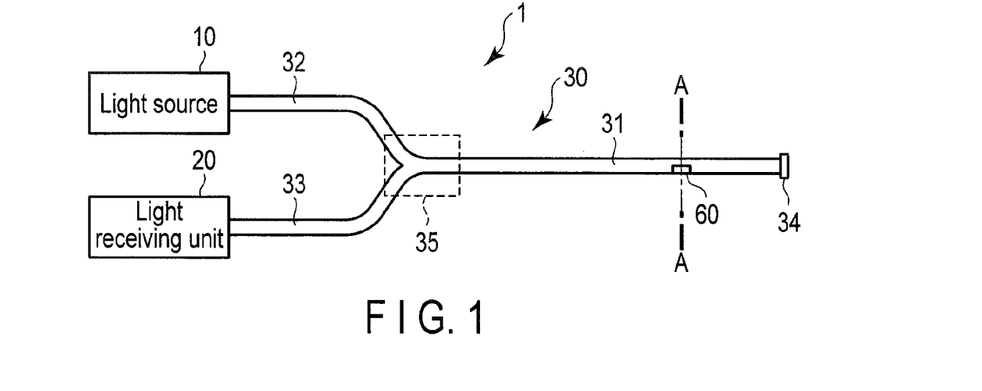
FIG. 1 is a schematic diagram of a light guide sensor according to a first embodiment.

As shown in FIG. 1, the light guide sensor 1 according to the first embodiment comprises a light source 10 which emits light, a light guide member 30 which has an elongated shape and which guides the light emitted from the light source 10, and a light receiving unit 20 which receives the guided light.

The light source 10 is, for example, a light emitting diode (LED) or a laser light source.

Figure 2:
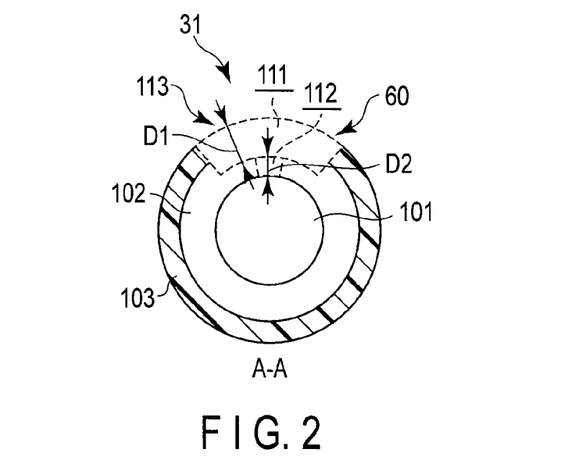
FIG. 2 is a cross sectional view of a detecting portion in the light guide sensor according to the first embodiment.

The light guide member 30 comprises a detection light guide member 31, a light-supply light guide member 32, and a light-receiving light guide member 33 which branch into three parts in a joint 35 and which extend to constitute a Y-shape, and a reflecting portion 34 which is provided at the end of the detection light guide member 31 to reflect the guided light. Here, the light guide member 30 is, for example, an optical fiber, and comprises a core 101, and a cladding 102 covering the outer circumference of the core 101, as shown in FIG. 2. The light guide member 30 may further have a cover 103 as outermost packing. The core 101 is made of, for example, a material which is more resistant to heat and mechanical external force than the cladding 102 and/or the cover 103. Moreover, in the present embodiment, the light guide member 30 may be, for example, a slab light guide instead of the optical fiber.

The light-supply light guide member 32 is a light guide in the light guide member 30, and guides the light emitted from the light source 10 provided at the end to the joint 35. The joint 35 is formed by connecting two light guide members to one light guide member. The joint 35 has the function to guide most of the light entering from the light-supply light guide member 32 to the detection light guide member 31, and guide at least some of the light reflected by the reflecting portion 34 to the light-receiving light guide member 33.

The detection light guide member 31 follows the flexible action of the measurement target, and has an end face (the reflecting portion 34) which reflects light to the end to let the light come and go. That is, the detection light guide member 31 guides the light coming from the light-supply light guide member 32 via the joint 35 to the reflecting portion 34, and guides the reflected light reflected by the reflecting portion 34 back to the joint 35.

The light-receiving light guide member 33 is a light guide in the light guide member 30, and guides the reflected light reflected by the reflecting portion 34 and branched in the joint 35 to the light receiving unit 20 provided at the end.

The detection light guide member 31 has at least one detecting portion 60.

As shown in FIG. 2, the detecting portion 60 has a thin film portion 111 which is a first opening where at least part of the cladding 102 is removed from the outer circumference of the detection light guide member 31, an opening 112 which is a second opening formed within the range of the thin film portion 111 where the core 101 is exposed, and an optical characteristic converting member 113 disposed in the thin film portion 111 and the opening 112. The detecting portion 60 does not require the core 101 to be exposed as long as the light passing through the light guide reaches the opening 112. Hereinafter, the surface close to the core 101 in the thin film portion 111 and the opening 112 is referred to as a bottom surface. The thin film portion 111 is a groove (hole) cut by desired energy along the surface of the core 101. Here, the desired energy is, for example, force that does not damage the core 101 in one processing.

The processing includes, for example, laser, heat, pressure, etching, and machining processing. Here, in the laser processing, for the light guide member 30, the output of laser is adjusted, and the cladding 102 and the cover 103 are only removed. In the heat processing, for the light guide member 30, the difference of heat resistance between the core 101, the cladding 102, and the cover 103 is used or the quantity of heat is adjusted to only remove part of the cladding 102 and the cover 103 by heating. In the pressure processing, for the light guide member 30, the difference of strength between the core 101, the cladding 102, and the cover 103 is used or the pressure is adjusted to only remove the cladding 102 and the cover 103 by pressurization. In the etching processing, for the light guide member 30, a material or a chemical that only etches the cladding 102 and the cover 103 is selected to only remove part of the cladding 102 and the cover 103.

The thin film portion 111 is formed with a depth D1 at which the cover 103 and part of the cladding 102 are removed to leave a cladding thickness such that the light guide amount hardly changes even by bending. The thin film portion 111 may be formed by more than one step rather than by one step in the diametrical direction.

Figure 3:
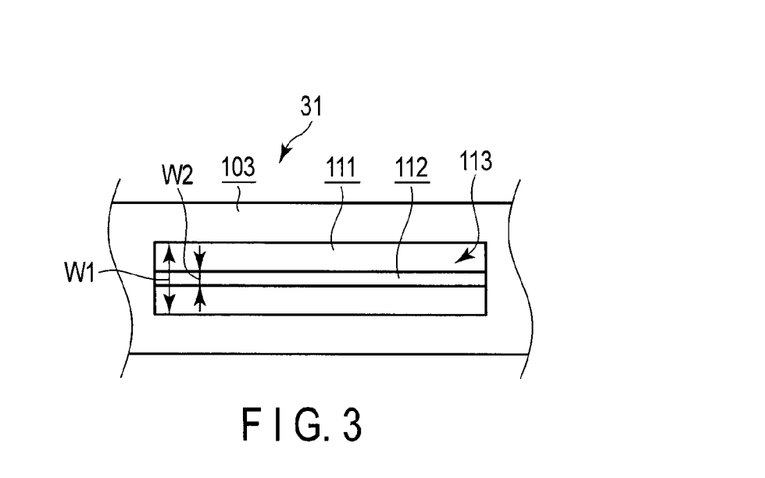
FIG. 3 is a top view of a detecting portion.

The opening 112 is formed in the thin film portion 111 with a depth D2 by desired energy, and is a closed-end hole formed so that the outer circumferential surface of the core 101 is exposed. As shown in FIG. 3, the opening 112 has a predetermined elongated shape. The predetermined elongated shape is a closed-end hole having a small width for the light guide member 30 suited to detect the direction and shape of the bending of the light guide member 30. For example, a width W2 of the opening 112 is formed to be smaller than a width W1 of the thin film portion 111.

Here, there is a difference of height between the thin film portion 111 and the opening 112. The difference of height is, for example, a step with a rack between the thin film portion 111 and the opening 112, or is a shape smoothly tilted from the thin film portion 111 to the opening 112.

The opening 112 is preferably formed so that the depth D2 is smaller than the width W2 of the opening 112 to ensure that the optical characteristic converting member 113 is disposed. The opening 112 may be formed by more than one layer in the diametrical direction.

The optical characteristic converting member 113 has the function to convert the characteristics of the guided light. The optical characteristic converting member 113 is, for example, a light guide loss member or a wavelength converting member. For example, the light guide loss member includes a light absorber, and the wavelength converting member includes a fluorescent material. In the present embodiment, the optical characteristic converting member is treated as the light guide loss member. The optical characteristic converting member 113 is disposed in at least the opening 112, and may further reach the thin film portion 111. The optical characteristic converting member 113 has viscosity that ensures the optical characteristic converting member 113 to be disposed in the elongated opening 112.

In the light guide sensor 1, the outer circumferential part of the detecting portion 60 is initially deformed, for example, thermally deformed, pressed, or cut by a known processing method so that the light guided by the core 101 does not leak, and the thin film portion 111 which is a recessed groove is thus formed. The cutting amount is then adjusted so that the elongated hole which leaks the light guided by the core 101 is opened within the range of the thin film portion 111 along the longitudinal direction of the light guide sensor 1, and the opening 112 is formed.

Finally, the optical characteristic converting member 113 is disposed in at least part of the opening 112 to convert the characteristics of the light which has leaked from the core 101. The optical characteristic converting member 113 may be formed to pass over the thin film portion 111 as long as the optical characteristic converting member 113 is disposed inside the outer circumferential part of the light guide sensor 1.

The light radiated from the light source 10 is guided through the light-supply light guide member 32, the joint 35, and the detection light guide member 31, and reflected by the reflecting portion 34. The reflected light reflected by the reflecting portion 34 is branched in the joint 35 as detected light, and guided through the light-receiving light guide member 33 and then reaches the light receiving unit 20. The light receiving unit 20 photoelectrically converts the received detected light, and outputs an electric signal indicating a light amount.

Figure 4A:
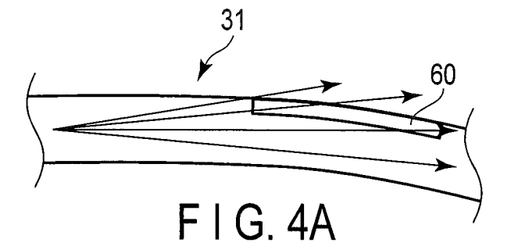
FIG. 4A is a schematic diagram of the operation of the light guide sensor bent in a direction in which the conversion amount of light amount is great.

In the present embodiment, the light guided through the light guide member 30 is lost when entering the optical characteristic converting member 113. This light guide loss amount changes depending on the bending of the detection light guide member 31, the twisting direction, and the bending amount as shown in FIG. 4A, FIG. 4B, and FIG. 4C.

Figure 4B:
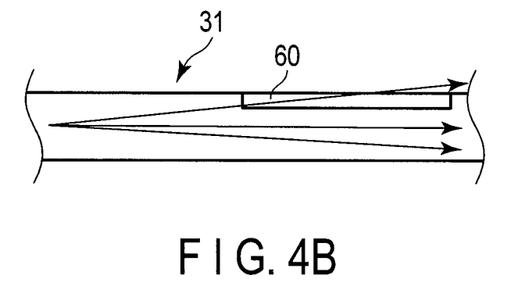
FIG. 4B is a schematic diagram of the operation of the linear light guide sensor to be the reference for the conversion amount of light amount.
Figure 4C:
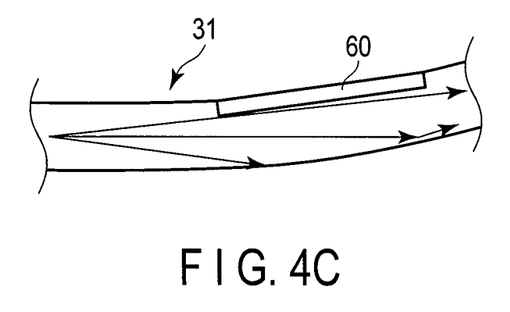
FIG. 4C is a schematic diagram of the operation of the light guide sensor bent in a direction in which the conversion amount of light amount is small.

As shown in FIG. 4B, a certain amount of light is lost in the optical characteristic converting member 113 in accordance with the width W2 of the opening 112 even if the detection light guide member 31 is straight. On the basis of this light loss amount, if the optical characteristic converting member 113 is disposed on the outer circumferential surface in the bending direction of the bending detection light guide member 31, for example, as shown in FIG. 4A, a light guide loss amount greater than the reference light guide loss amount in FIG. 4B is produced. In contrast, if the optical characteristic converting member 113 is disposed on the inner circumferential surface in the bending direction of the bending detection light guide member 31, a light guide loss amount smaller than the reference light guide loss amount in FIG. 4B is produced. In this instance, the width W2 of the opening 112 is formed to be small, so that even if the detection light guide member 31 is bent and/or twisted, the directions in which reactions are made are limited.

This change of the light guide loss amount is reflected in the amount of the detected light received by the light receiving unit 20. That is, the change is reflected in the output signal of the light receiving unit 20. Therefore, the bending direction and the bending amount (angle) at the position where the light guide sensor, that is, the optical characteristic converting member 113 of the measurement target is provided can be detected by the output signal of the light receiving unit 20. Since the width W2 of the opening 112 formed within the range of the thin film portion 111 where the light from the core is not transmitted is formed to be small, the light guide sensor 1 can obtain a light guide amount change greater than the reference light guide loss amount in the event of bending.

Since the thin film portion 111 is formed with the depth D1 such that the cladding 102 is sufficiently thin, the thin film portion 111 can be processed by low energy. Moreover, there are many processing methods available, and the small opening 112 having the width W2 can be easily formed.

According to the present embodiment, the width W2 of the opening 112 is formed to be small, so that the light guide sensor 1 can detect with precision because the directions in which the detection light guide member 31 reacts to bending and/or twisting are limited.

The locations of the thin film portion 111 and the opening 112 can be easily distinguished from the surrounding because of their difference of height, and the detecting portion 60 can be used as a mark for the location of the optical characteristic converting member 113.

In the detecting portion 60, the depths D1 and D2 and the widths W1 and W2 of the thin film portion 111 and the opening 112 can be suitably set and shaped during formation. For example, the depth D1 of the thin film portion 111 can be greater than the depth D2 of the opening 112. That is, the thin film portion 111 can be formed at such depth that most of the cladding 102 is removed without exposing the core. In this case, the thickness of the cladding 102 is sufficiently small as compared with the thickness of the surrounding cover 103 and/or the cladding 102. Therefore, the opening 112 can be formed by low-energy processing.

The width W1 of the thin film portion 111 can be formed to be greater than the sum of the depths D1 and D2 of the thin film portion 111 and the opening 112 by low-energy processing.

In this case, first, the width W1 of the thin film portion 111 is widely formed in the outer circumference of the detection light guide member 31 so that the width W1 is greater than the sum of the depths D1 and D2 of the thin film portion 111 and the opening 112, and then the width W2 of the opening 112 is formed to be smaller than the width W1 of the thin film portion 111. In this instance, the width W1 of the thin film portion 111 is great, so that it is possible to reduce the burden of finely adjusting energy associated with the processing of the opening 112 in the region of the thin film portion 111, and the formation of the opening 112 is easier.

In this case, it is preferable that the thin film portion 111 is first widely formed in the outer circumference of the detection light guide member 31 by low-energy processing, and a hole having a small width is then further formed step by step in the region of the thin film portion 111 by low-energy processing. As a result of the repeated processing, the opening 112 is finally formed. This formation method includes processing with low energy, so that the shape of the opening 112 can be finely formed. For example, the opening 112 is formed into an elongated shape having the sufficiently small width W2.

A modification of the first embodiment is described.

Figure 5:
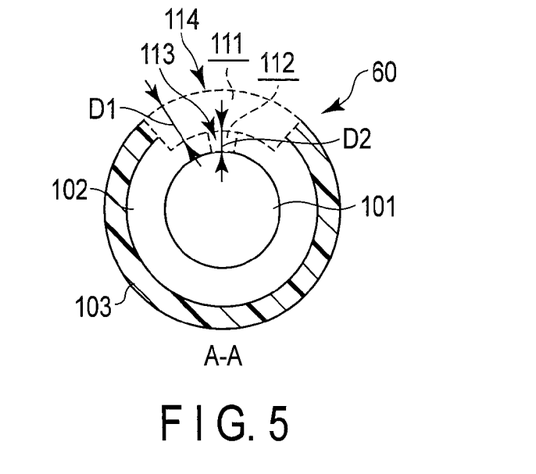
FIG. 5 is a cross sectional view of the light guide sensor according to a third modification of the first embodiment.

The light guide sensor 1 according to the modification of the first embodiment is substantially similar to the light guide sensor 1 according to the first embodiment, but is different in that the optical characteristic converting member 113 is coated with a protective material 114.

As shown in FIG. 5, in the detecting portion 60 according to the modification of the present embodiment, the thin film portion 111 is coated with the protective material 114 to protect the optical characteristic converting member 113 and the detection light guide member 31.

According to the modification of the present embodiment, the thin film portion 111 is widely formed, so that the protective material 114 can be easily disposed. Because of the coating protective material, deterioration of the optical characteristic converting member 113 and the detection light guide member 31 can be prevented.

[Second Embodiment]

Figure 6:
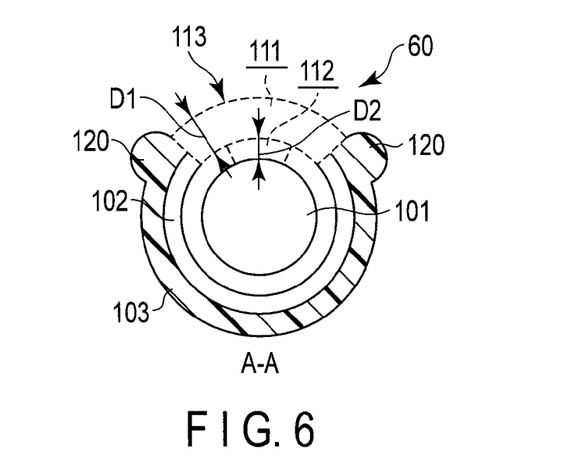
FIG. 6 is a cross sectional view of the detecting portion of the light guide sensor according to a second embodiment.

The light guide sensor 1 according to the present embodiment is substantially equivalent to the sensor structure according to the first embodiment described above, but is different in, for example, the structure of the detecting portion 60.

The core 101 according to the present embodiment is made of, for example, a material that is highly resistant to light or heat.

The cladding 102 and the cover 103 according to the present embodiment are made of, for example, resin materials.

As shown in FIG. 6, the detecting portion 60 according to the present embodiment is formed to have projections 120 at the ends, for example, four ends of the thin film portion 111 and/or the opening 112. The projections 120 are, for example, bulges formed at the ends during laser processing or heat processing, or burrs formed during machining processing.

The side surfaces of the thin film portion 111 according to the present embodiment constitute parts of the projections 120, and are formed smooth. For example, the thin film portion 111 is formed by using the light or heat of laser to remove the cladding 102 and the cover 103.

The projections 120 have smooth shapes formed, for example, when the resin material removed during the formation of the thin film portion 111 is cooled and solidified at the ends. The projections 120 may have cornered shapes.

Since the core 101 is highly resistant to heat, the cladding is only removed by the adjustment of the heat quantity to be applied when the opening 112 is formed in the thin film portion 111. The projections 120 prevent the optical characteristic converting member 113 or the protective material 114 from sticking out when the optical characteristic converting member 113 or the protective material 114 is disposed in the thin film portion 111.

According to the present embodiment, the cover 103 and part of the cladding 102 alone can be easily removed by the adjustment of the heat quantity. Since the projections 120 are formed, the location of the detecting portion 60 can be easily recognized. Therefore, the detecting portion 60 is disposed in the proper position of the measurement target. Moreover, when the detecting portion 60 contacts the measurement target by the projections 120, the projections 120 come into contact instead of the optical characteristic converting member 113, so that abrasion of the optical characteristic converting member 113 can be prevented. The optical characteristic converting member 113 or the protective material 114 can be easily disposed in the thin film portion 111 so that the projections 120 serve as embankments.

Now, a first modification of the second embodiment is described.

Figure 7:
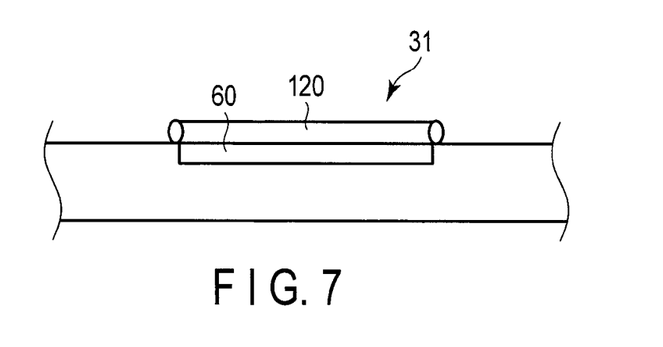
FIG. 7 is a longitudinal sectional view of the detecting portion of the light guide sensor according to a first modification of the second embodiment.

The configuration of the light guide sensor 1 according to the first modification of the second embodiment is substantially equivalent to that of the light guide sensor 1 according to the second embodiment. However, the detecting portion 60 is formed to be longer in the longitudinal direction. Therefore, equivalent components are provided with the same reference numbers and are not described in detail.

As shown in FIG. 7, the detecting portion 60 according to the first modification of the second embodiment is formed along the longitudinal direction in the outer circumferential portion of the light guide member 31.

The detecting portion 60 according to a second modification is disposed in accordance with the proper position of the measurement target. The opening 112 can be formed to have a larger area while maintaining its width.

In the second modification, the detecting portion 60 can adjust the light guide loss amount while maintaining the detection accuracy for the bending of the measurement target.

The second modification of the second embodiment is described.

The configuration of the light guide sensor 1 according to the second modification is substantially equivalent to that of the light guide sensor 1 according to the first modification of the second embodiment. However, the shape of the detecting portion 60 in the longitudinal direction is defined.

The detecting portion 60 according to the second modification is formed into such a shape that the width in the longitudinal direction is constant or the width is not extremely increased at the end in the longitudinal direction. This detecting portion 60 is formed with substantially uniform width in the longitudinal direction, which ensures that the amount of loss varies in the optical characteristic converting member 113 by the degree of bending and/or twisting. Therefore, the detection accuracy for the bending of the measurement target is improved.

A third modification of the second embodiment is described.

Figure 8:
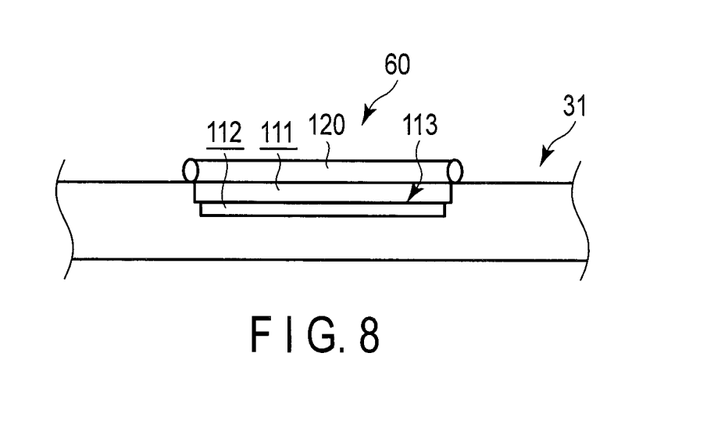
FIG. 8 is a longitudinal sectional view of the detecting portion of the light guide sensor according to a third modification of the second embodiment.

The configuration of the light guide sensor 1 according to the third modification is substantially equivalent to that of the light guide sensor 1 according to the first modification of the second embodiment. However, the length of the opening 112 is defined. Therefore, equivalent components are provided with the same reference numbers and are not described in detail.

As shown in FIG. 8, the opening 112 according to the present embodiment is formed to be shorter than the thin film portion 111 in the longitudinal direction. In the third modification, the opening 112 can be accurately formed in accordance with the longitudinal length of the previously formed thin film portion 111, so that more than one opening 112 having substantially uniform length can be formed. Thus, when more than one detecting portion 60 is disposed in the detection light guide member 31, constant detection accuracy of each detecting portion 60 is maintained.

A fourth modification of the second embodiment is described.

Figure 9:
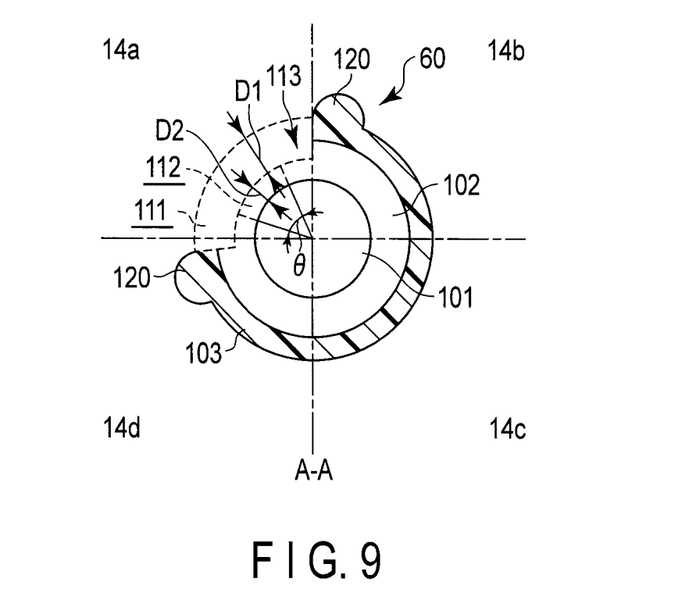
FIG. 9 is a cross sectional view of the detecting portion of the light guide sensor according to a fourth modification of the second embodiment.

In the fourth modification, the section of the detection light guide member 31 perpendicular to the optical axis is divided into four regions which are defined as a first quadrant 14a, a second quadrant 14b, a third quadrant 14c, and a fourth quadrant 14d.

In the fourth modification, the configuration of the light guide sensor 1 is substantially equivalent to that of the light guide sensor 1 according to the first modification of the second embodiment. However, the opening angle of the opening 112 is defined. Therefore, equivalent components are provided with the same reference numbers and are not described in detail.

As shown in FIG. 9, the opening 112 according to the present embodiment is formed so that an opening angle $2\theta$ which is the angle of the opening width originating in the center of the detection light guide member 31 is less than 90°. When the opening 112 is disposed in each of the adjacent regions, the openings 112 disposed in two regions are arranged without overlap. The opening 112 is disposed in at least one quadrant. For example, the opening 112 is disposed in the first quadrant 14a.

In the fourth modification, the opening angle 2θ is defined so that the uniform width of the opening 112 can be formed. Thus, the detection accuracy of the light guide sensor 1 can be uniform regardless of the processing methods and steps. When one opening 112 is disposed in each of the four regions, the bending of the measurement target in four directions can be detected. The bending direction of the measurement target can be easily recognized by changing the opening angle 2θ of the opening 112 disposed in each region. In the fourth modification, more than one opening 112 may be formed in each quadrant and have opening angles that do not overlap.

A fifth modification of the second embodiment is described.

Figure 10:
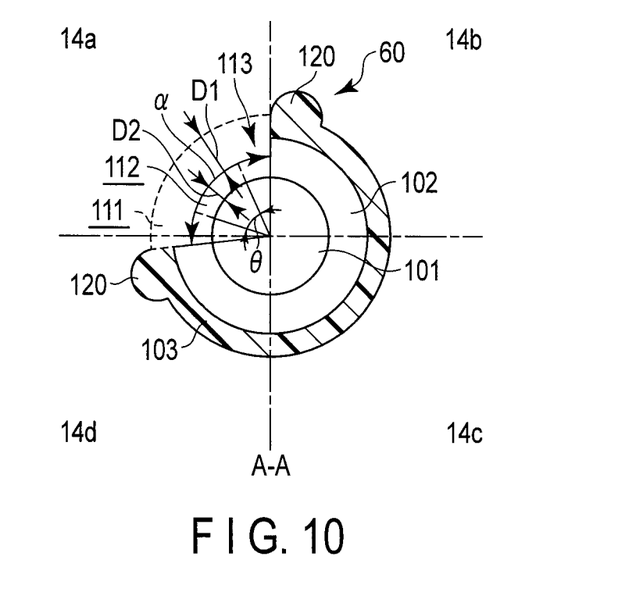
FIG. 10 is a cross sectional view of the detecting portion of the light guide sensor according to a fifth modification of the second embodiment.

The configuration of the light guide sensor 1 according to the fifth modification is substantially equivalent to that of the light guide sensor 1 according to the fourth modification of the second embodiment. However, the opening angle θ of the opening 112 is formed to be smaller than the opening angle θ of the thin film portion 111. Therefore, equivalent components are provided with the same reference numbers and are not described in detail.

As shown in FIG. 10, the opening 112 according to the fifth modification is formed so that the opening angle α which is the angle of the opening width in the thin film portion 111 is smaller than the opening angle θ.

In the fifth modification, the opening angle θ of the opening 112 is formed to be smaller than the opening angle α of the thin film portion 111, so that the opening 112 having predetermined detection accuracy for the bending of the measurement target can be easily formed.

A sixth modification of the second embodiment is described.

Figure 11:
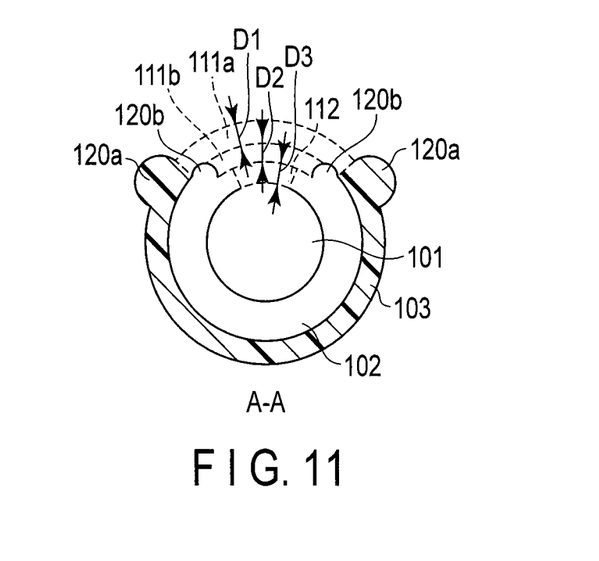
FIG. 11 is a cross sectional view of the detecting portion of the light guide sensor according to a sixth modification of the second embodiment.

The light guide sensor 1 according to the sixth modification is substantially equivalent to the light guide sensor 1 according to the second embodiment. However, the thin film portion 111 is formed to have multiple layers. Therefore, equivalent components are provided with the same reference numbers and are not described in detail.

As shown in FIG. 11, the detecting portion 60 according to the present embodiment has more than one thin film portion 111 and more than one projection 120. For example, the detecting portion 60 has a plurality of thin film portions 111a and 111b and a plurality of projections 120a and 120b.

The thin film portion 111a is formed by low energy. For example, the thin film portion 111a is formed by heat treatment processing with a small heat quantity. At this time, the projection 120a is formed at the end. The thin film portion 111b is formed within the range of the thin film portion 111a, and the projection 120b is similarly formed at the end. The opening 112 is formed within the range of the thin film portion 111b. At this time, the thin film portion 111a is formed with the depth D1, the thin film portion 111b is formed with the depth D2, and the opening 112 is formed with the depth D3.

When the detection light guide member 31 contacts the measurement target, the projection 120a is applied as a protective member of the detecting portion 60. The projection 120b is applied as a guide when the optical characteristic converting member is disposed in the opening 112.

In the fifth modification, the projections 120a and 120b prevent, for example, the optical characteristic converting member 113 or the protective member from sticking out. When the projections 120a and 120b are formed in different parts, the optical characteristic converting member 113 can be easily disposed in the opening 112 because of the projection 120b at the end of the opening 112. It is also possible to prevent the detecting portion 60 from directly contacting the measurement target.

In the previously described embodiments, more than one detecting portion 60 may be disposed.

Furthermore, in the configurations described by way of example in the previous embodiments, the optical fiber joint is provided, and light is reflected by the end surface (the reflecting portion) so that the light is guided in and out inside one optical fiber (the detection optical fiber). However, this is not a limitation. For example, it should be understood that the present invention can also be easily applied to a transmission/light guide type fiber sensor including a light source provided at one end of a fiber, an optical fiber which guides the emission light from the light source, and a light receiving unit provided at the other end of the fiber opposite to the light source, wherein these components are linearly arranged.

REFERENCE SIGNS LIST

1: light guide sensor, 10: light source, 14a: first quadrant, 14b: second quadrant, 14c: third quadrant, 14d: fourth quadrant, 20: light receiving unit, 30: light guide member, 31: detection light guide member, 32: light-supply light guide member, 33: light-receiving light guide member, 34: reflecting portion, 35: joint, 60: detecting portion, 101: core, 102: cladding, 103: cover, 111, 111a, 111b: thin film portion, 112: opening, 113: optical characteristic converting member, 114: protective material, 120, 120a, 120b: projection, θ: opening angle of opening, α: opening angle of thin film portion, D1: depth of thin film portion, D2: depth of opening, W1: width of thin film portion, W2: width of thin film portion.

What is claimed is:
1. A light guide sensor comprising:
a light source;
a light guide member elongated in a longitudinal direction, the light guide member comprising a core which guides light radiated from the light source, a cladding formed around the core, and at least one detecting portion; and
a light receiving unit which receives the light that has been guided by the light guide member and has passed via the detecting portion,
wherein the detecting portion having a first opening formed by removal of at least part of the cladding resulting in the cladding having a first thickness at the first opening in a thickness direction perpendicular to the longitudinal direction such that the cladding having the first thickness is sufficient so as to not transmit the light from the core, the detecting portion further having a second opening which is formed in the cladding having the first thickness and within a width of the first opening, the width being in a direction perpendicular to the thickness direction, the second opening one of exposing the core or resulting in a second thickness of the cladding sufficient so as to transmit the light from the core.

2. The light guide sensor according to claim 1, wherein the detecting portion has a difference of height in the thickness direction between the first opening and the second opening.

3. The light guide sensor according to claim 1, wherein the second opening is formed so that the core is exposed.

4. The light guide sensor according to claim 1, wherein a depth of the first opening in the thickness direction is greater than a depth of the second opening in the thickness direction.

5. The light guide sensor according to claim 4, wherein the detecting portion is formed so that the width of the first opening in the direction perpendicular to the longitudinal direction is greater than a sum of the depths of the first opening and the second opening.

6. The light guide sensor according to claim 4, wherein the depth of the second opening is smaller than a width of the second opening in the direction perpendicular to a longitudinal direction.

7. The light guide sensor according to claim 1, wherein the detecting portion comprises a projection in an outer circumference of at least one of the first opening and the second opening.

8. The light guide sensor according to claim 7, wherein the projection is formed to bulge in an outer circumferential portion of the light guide member.

9. The light guide sensor according to claim 8, wherein the core is more resistant to heat and external force than the cladding.

10. The light guide sensor according to claim 7 or 8, wherein the projection comprises a first projection formed at an end of the first opening and a second projection formed at an end of the second opening, wherein the first projection is formed higher than the second projection in the thickness direction.

11. The light guide sensor according to any one of claims 7 to 9, wherein the detecting portion comprises an optical characteristic converting member which converts the characteristics of light in at least part of the second opening without passing over the projection.

12. The light guide sensor according to claim 1, wherein the light guide member is an optical fiber having a cover further surrounding the cladding, and
the first opening is formed by removing at least part of the cover.

13. The light guide sensor according to claim 1, wherein the detecting portion is elongated in the longitudinal direction of the light guide member.

14. The light guide sensor according to claim 13, wherein the second opening has a length in the longitudinal direction less than or equal to a length of the first opening in the longitudinal direction.

15. The light guide sensor according to claim 12, wherein the core, the cladding, and the cover are concentrically arranged in a section perpendicular to an optical axis, and a first angle defined by a straight line connecting a center of the core to each side surface of the second opening is 90° or less.

16. The light guide sensor according to claim 15, wherein a second angle formed by a straight line connecting the center to each side surface of the first opening is formed to be equal to or more than the first angle.

17. The light guide sensor according to claim 1, wherein the first opening having a larger dimension in the width direction at an outer surface of the cladding than at other portions of the first opening.

18. A method of forming a detecting portion of a light guide sensor, the light guide sensor comprising a flexible light guide member elongated in a longitudinal direction, the light guide member having a core which guides light radiated from a light source and a cladding surrounding the core, at least one detecting portion being formed in the cladding and disposed at a detection position of a measurement target; and a light receiving unit which receives the light guided by the light guide member, the method comprising:
forming a first opening by deforming at least part of the cladding into a recessed shape resulting in the cladding having a first thickness at the first opening in a thickness direction perpendicular to the longitudinal direction such that the cladding having the first thickness is sufficient so as to not transmit light at the detection position of the detecting portion; and
forming a second opening deformed into a recessed shape, the second opening being deformed in the cladding having the first thickness and within a width of the first opening, the width being in a direction perpendicular to the thickness direction, the second opening one of exposing the core or resulting in a second thickness of cladding sufficient so as to transmit the light from the core.

19. The method of forming the detecting portion of the light guide sensor according to claim 18, wherein the forming of the second opening comprises removing part of the outer circumferential surface of the core.

20. The method of forming the detecting portion of the light guide sensor according to claim 18, wherein the forming of the first opening and the forming of the second opening each comprise applying any one of heat, light, and mechanical external force to the light guide member.

21. The method of forming the detecting portion of the light guide sensor according to claim 18, wherein the forming of the first opening further comprises forming a projection having a bulging shape at an end of the first opening.

22. The method of forming the detecting portion of the light guide sensor according to claim 18, further comprising, after the forming the first opening, disposing an optical characteristic converting member at least partially in the first opening which converts the characteristics of light inside the projection without passing over the projection.

* * * * *